United States Patent [19]

Bácskai et al.

[11] Patent Number: 4,694,479
[45] Date of Patent: Sep. 15, 1987

[54] VIDEO-RADIOGRAPHIC PROCESS AND EQUIPMENT FOR A QUALITY CONTROLLED WELD SEAM

[75] Inventors: Endre Bácskai; Ferenc Rétfalvi; András Sásdi, all of Budapest, Hungary

[73] Assignee: Kohaszati Cyaropito Vallalat Gepipari Technologiai Intezet, Budapest, Hungary

[21] Appl. No.: 728,499

[22] Filed: Apr. 29, 1985

[51] Int. Cl.[4] .............................................. G01N 23/02
[52] U.S. Cl. ......................................... 378/58; 378/59; 378/99; 358/111
[58] Field of Search ....................... 378/58, 59, 61, 99; 358/111

[56] References Cited

U.S. PATENT DOCUMENTS

| | | | |
|---|---|---|---|
| 2,900,513 | 8/1959 | Duffy | 378/59 |
| 3,924,064 | 12/1975 | Nomura et al. | 378/99 |
| 4,409,616 | 10/1983 | Ledley | 358/111 |
| 4,415,980 | 11/1983 | Buchanan | 358/111 |
| 4,549,306 | 10/1985 | Shideler et al. | 378/58 |

FOREIGN PATENT DOCUMENTS

| | | | |
|---|---|---|---|
| 83/01509 | 4/1983 | PCT Int'l Appl. | 378/59 |
| 1147961 | 3/1985 | U.S.S.R. | 378/58 |

*Primary Examiner*—Craig E. Church
*Assistant Examiner*—John C. Freeman
*Attorney, Agent, or Firm*—Gabriel P. Katona

[57] ABSTRACT

A weld inspection process and an associated system for the determination and assessment of weld seams by first producing a flawless weld seam on a test specimen, making a point by point inspection of the test specimen using a pair of alternately pulsed X-ray or gamma ray sources, while generating signals which may be simultaneously displayed and stored, to form a permanent record of the test specimen weld seam, on a target plate. A point by point comparison of is made of a new, similar weld and the recorded image is instantaneously compared with the previously recorded, stored image of the flawless test weld. In the event of identical images, that point of the weld is deemed flawless, while a lack of identity indicates a flaw, in which event, the defective position is marked for subsequent repair, removal or total rejection.

3 Claims, 3 Drawing Figures

VIDEO-RADIOGRAPHIC PROCESS AND EQUIPMENT FOR A QUALITY CONTROLLED WELD SEAM

FIELD OF THE INVENTION

This invention relates, in general, to the welding arts, and, more particularly to a process and the associated system for the determination and assessment of the quality of weld seams and the spatial location of defects with the use of an X-ray or gamma source and a closed-circuit TV network.

BACKGROUND OF THE INVENTION

As is familiar, the quality of weld seams is checked by a radiographic procedure involving the X-raying of the seam and making a radiograph thereof. The film is developed and assessed as a documentary evidence of seam quality. Furthermore, other devices are available, by which the radiograph can be displayed on a closed-circuit TV set. However, this arrangement is usually not accepted as a document although the video display can be recorded on a magnetic tape and reproduced subsequently in the desired number.

However, none of these procedures ensures the determination of the true special image of the defect although e.g. a spherical inclusion is sometimes acceptable, but a flat sharp-contured one is not; both inclusions having the same radiographic image, both are graded as reparable.

Another point of relevance is the surface of seam to which the defect lies closer, from which the scraping is to be started for the subsequent correction. Thus there is an unequivocal need for exact data on the spatial location, size and configuration of weld defects. The currently known procedures are unfit for this purpose.

One object of our invention is the realization of a process, together with it's associated system, by which the spatial location, configuration and size of weld defects can be determined and which, furthermore, enable a quality control with documentary records.

Accordingly, our invention is a videographic process as procedure for the quality control of weld seams, involving the transillumination, point by point, of the weld seam of the test specimen with X-ray or gamma rays. Electrical signals are generated to represent the radiographic image of the weld and its surrounding. The radiograph is recorded and displayed simultaneously, the image is assessed, and the procedure is started all over again in the next point. The essential feature of the invention is the use of two radiation sources of identical intensity arranged symmetrically about the vertical axis, perpendicular to the longitudinal axis of the weld seam. The target plate of the video camera is arranged symmetrically to the vertical axes mention above, parallel to the longitudinal and the transversal exceeds in the area to be irradiated, in such a way that the axes of the radiation sources are aligned with the axis of the target plate. The first radiation source is operated in pulsed mode and the radiographic still picture obtained is converted into electric signals, and this first picture is stored away. Then the second radiation source is operated in a pulsed mode. The resulting picture is similarly converted into electrical signals, stored, and the two memorized images are compared each to a standard image recorded of a perfect weld of identical parameters previously recorded with this procedure. In the case of identity, the weld detail is graded flawless, whereas it is rejected if a difference is found.

The size of the first projected image on the transversal axis is determined in the first radiograph, the second projection of the defect being determine in the second one. Then the coordinates of the defect are computed as described below.

$$X_o = L \frac{x' + x''}{x' - x'' + 2L}$$

$$Y_o = M + V - \frac{M + V + \Delta'}{X' + L}(L + X_O)$$

where
 L = half of the distance between radiation source,
 M = height of radiation source above the weld,
 V = thickness of weld seam,
 $\Delta'$ = distance of the target plate below the weld seam
 $x'$ = the displacement of the first defect image from a given (Y) axis,
 $x''$ = the displacement of the second defect image from the given (Y) axis.

The defect coordinates obtained are noted, and so is the number of steps along the longitudinal axis as the third defect coordinate, and the test equipment is advanced by one step along the longitudinal axis parallel to itself. The steps of the procedure are repeated over and over again along the entire length of the weld.

Furthermore, our invention is embodied in a system for testing weld seams, involving a radiation source above the specimen carrying the weld, and a video camera under it. A picture display, a video storage and a computer (arithmetic unit) are attached to the video camera. The essential feature of the invention is the use of a second radiation source above the target specimen, the axes of the first and the second radiation sources and of the video camera coinciding in the same plane; they are secured to an actuation device, and the radiation sources are arranged symmetrically to the axis of the weld. Pointing downward at an angle, this arrangement complies with the formulae $$\frac{t}{2} = -/\Delta' + V/\frac{2L+g}{2M} - \frac{g}{2}$$

$$\frac{K}{2} > \frac{G}{2} > \frac{g}{2}$$

$$Y_k > V\Delta' > \Delta$$

where
 t = diameter of target plate,
 $\Delta'$ = distance of target from the lower plane of the weld,
 V = thickness of weld,
 L = half-distance of radiation sources,
 M = elevation of the radiation source above the upper plane of the weld,
 g = thickness of weld,
 k = lower diameter of the irradiated space,
 G = upper diameter of the irradiated space,
 $Y_k$ = elevation of the intersection points of the conical ray beams above the weld,
 $\Delta$ = elevation of the intersection points of the conical ray beams beneath the weld.

Operated in pulsed mode, the radiation sources are connected to a control unit ensuring their alternating operation; a location signal source is connected to the actuation mechanism, the output of which is attached to the image storage, display and the arithmetic unit. Furthermore, it has a central control unit coordinating the functions of the subassemblies, with the outputs of the computer and the clock signal generator electrically connected to its inputs. The outputs of this central control unit are attached to the control inputs of the arithmetic unit, the radiation source control and the actuation device.

The equipment implementing our invention can be assembled practicably in such a way that the arithmetic unit includes a reference standard image storage, an image comparator, a provisional image storage ("latch"), a special-purpose computer, a data input unit and a defect storage. The video signal input of the arithmetic unit is connected to the signal inputs of the image comparator and provisional image storage; the output of the latter is connected to one data input of the special-purpose computer and to a signal input of the defect storage controlled by the special-purpose computer. The location signal input of the arithmetic unit is connected to the other data input of the special-purpose computer and to the other signal input of the defect storage; the output of the image comparator and the feedback output of the special-purpose computer are connected to the signal inputs of the central control unit. The control inputs of these units are connected to the control outputs of the central control unit; furthermore, the data input unit is connected to the basic data input of the special-purpose computer.

BRIEF DESCRIPTION OF THE DRAWING

Our invention is described in detail with reference to the Figures.

DETAILED DESCRIPTION OF THE INVENTION

Figure 1:
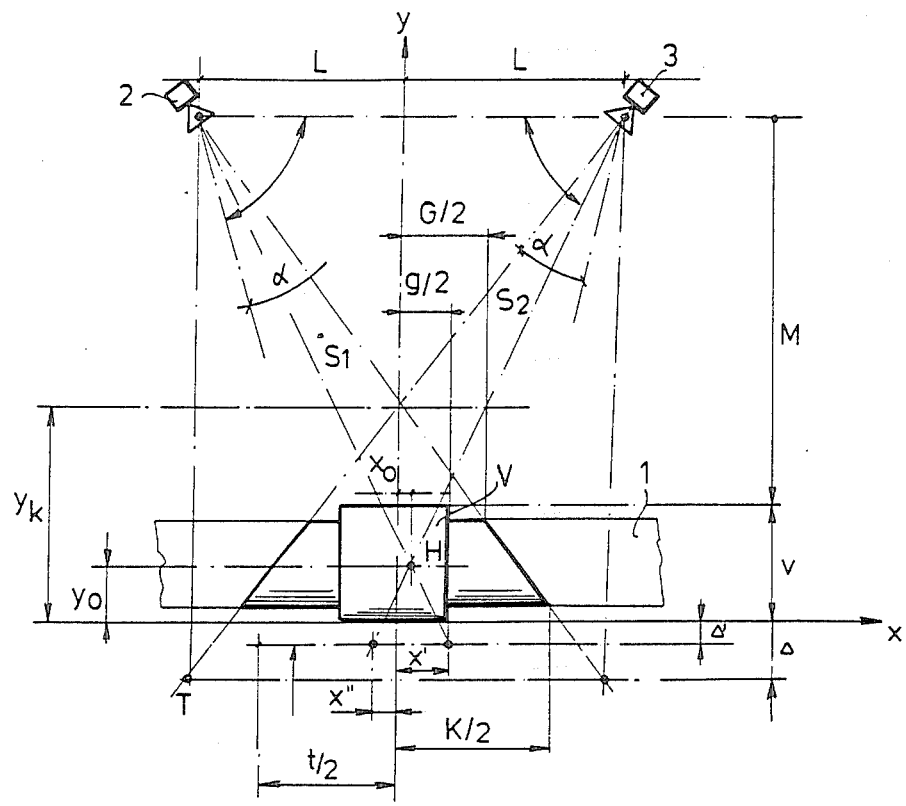
FIG. 1 shows the geometric of the test setup realizing the invention.
Figure 2:
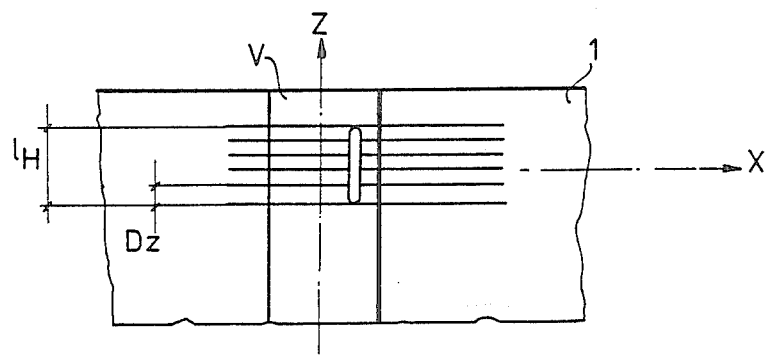
FIG. 2 shows the location of a defect along the weld.

As shown in FIG'S. 1, 2 and 3 the test setup representing our invention uses two radiation sources (2 and 3), pointing downward at an angle, at an elevation M above weld V of test specimen (1), located at distance L symmetrically from vertical axis Y of weld V. Operated alternately in a pulsed mode, radiation sources (1 and 2) will irradiate target specimen (1) in a conical angle α. Transverse axis X is arranged parallel to the plane of weld V, longitudinal axis Z is in a plane along the length and perpendicular to the transverse axis X while the vertical axis Y, as shown in FIGS. 1 and 2, is perpendicular to both the Z and Y axes. Weld V has a thickness of v and a thickness of g. The part of space irradiated by radiation sources (2 and 3) has an upper diameter of G and a lower diameter of K; the conical beams intersect one another at an elevation of $Y_k$. The image of defect H in weld V is formed by projection beams S1 and S2 on target plate T of t diameter of video camera (4) located at a distance of Δ' from the axis. The first and the second defect images (X' and X", respectively) are shown in the first and the second pictures, from which defect coordinates $X_o$ and $Y_o$ can be obtained with the formulae $$X_o = L \frac{X' + X''}{X' - X'' + 2L}$$

-continued $$Y_o = M + V - \frac{M + V + \Delta'}{X' + L}(L + X_o).$$

Defect coordinate $Z_o$ of defect H along axis Z is determined by advancing radiation sources (1 and 2) and video camera (4) parallel to themselves along axis Z in steps $D_Z$, and making a pair of radiographs in each position. Thus the unit step is $D_Z$, the sum of which (number of steps) defining length $l_H$ of defect H. The defect coordinates is $Z_o = l_H$, as can be seen in FIG. 2.

According to the invention, the procedure of checking weld V under test is as follows. With target object (1) placed under radiation sources (2 and 3) and over signal plate T of video camers (4), radiation sources (2 and 3) are operated in pulsed mode alternatingly, and the two radiographic still pictures are converted into electrical signals and stored away. Now each of the two memorized images is compared to a reference standard one picked up previously in the same manner, showing a flawless weld having the same parameters. In the case of an identity the weld detail is graded flawless. If a difference is found, the weld is graded defective, and defect coordinates $X_o$ and $Y_o$ are determined in the manner described earlier. At the same time, the serial number of step along the longitudinal axis is noted, and a unit step follows, with the procedure and the grading repeated. These procedure steps are repeated over and over again along the entire length of the weld.

Whenever a defect is found, the defective weld detail (g) is marked (e.g. with a paint) and given an identification number. This number is also recorded with the respective defect coordinates $X_o$, $Y_o$. In this way, each defective spot can be identified with a high accuracy. Knowing the images and coordinates of defects, the weld engineer can pass an unequivocal decision on the necessity and way of correction.

Since the flawless or defective nature of the weld can be documented unequivocally, the use of a radiographic film is dispensed with.

Figure 3:
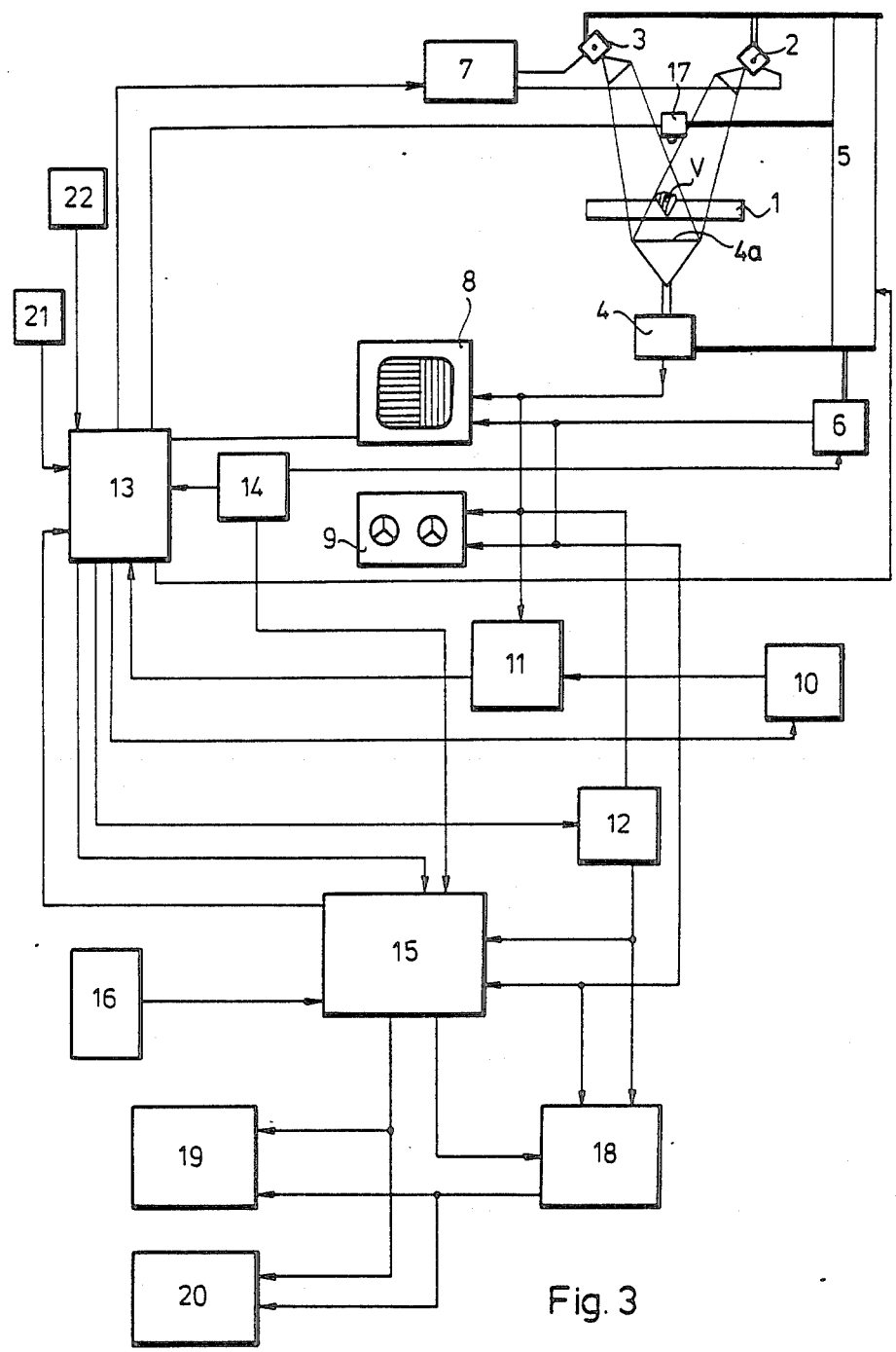
FIG. 3 shows the block diagram of the equipment representing the invention.

FIG. 3 shows the block diagram of an equipment representing a possible implementation of the procedure according to the invention.

Having weld V under test, target specimen (1) is arranged beneath radiation sources (2 and 3) and over target plate (4a) of video camera (4). The axes of radiation sources (2 and 3) are in a common plane with the axis of video camera (4)—all secured to a common actuation device (5). Spaced at 2L, pointing downward at an angle, radiation sources (2 and 3) are located symmetrically to vertical axis Y of weld V. An adequate functioning requires radiation sources (2 and 3), weld V and video camera (4) to be arranged in conformity with the relationships $$\frac{t}{2} = -(\Delta' + v)\frac{2L + g}{2M} - \frac{g}{2}$$

$$\frac{K}{2} > \frac{G}{2} > \frac{q}{2}, Y_k > V \text{ and } \Delta < \Delta'$$

where t=diameter of target plate (in video camera 4),
Δ=distance of the intersection point between the conical beams under the weld,
Δ'=distance of target plate from the lower plane of weld V, L = half-distance of radiation sources (2 and 3),
M = elevation of radiation sources (2 and 3) above the upper plane of the weld,
g = width of weld,
v = thickness of weld,
$Y_k$ = elevation of the intersection point between the conical beams of rays above the weld,
K = lower diameter of the irradiated area,
G = upper diameter of the irradiated area.

Radiation sources (2 and 3) are operated alternatingly in pulsed mode by radiation source control circuit (7). Actuation device (5) moves radiation sources (2 and 3), video camera (4) and defect-spot marker (17) jointly, parallel to themselves, along weld V. Attached to actuation device (5), location signal source (6) provides the marker signals for picture display (8), the picture storage, defect storage (18) and special-purpose computer (15). The output of video camera (4) is connected to the input of picture display (8); image storage (9) is connected to the input of image comparator (11) and provisional picture storage (12). Picked up in advance, the reference standard image is contained in reference standard picture storage (10), the output of which is connected to the other input of image comparator (11) (the output of the latter being connected to an input of central control unit 13). The output of provisional picture storage (12) is connected to the data input of special-purpose computer (15) and to the other signal input of defect storage (18) (the output of the latter being connected to defect display 19 and printer 20).

Data input unit (16) is connected to another data input of special-purpose computer (15) determining the coordinates of the defect, by which data can be entered concerning weld V under test. The data of special-purpose computer (15) are available on defect display (19) and printer (20); furthermore, it controls the operation of defect storage (18), and furnishes central control unit (13) with signal required for the coordinated operation of the equipment as a whole. Connected to the signal inputs of central control unit (13) are clock signal generator (14)—providing the clock signals of special-purpose computer (15) as well—, picture comparator (11), manual stepper (21) and manual-automatic selector (22).

At the same time, central control unit (13) controls and coordinates the operation of radiation source control circuit (7), actuation device (5), picture display (8), reference standard image storage (10), provisional image storage (12), spacial-purpose computer (15) and defect-spot marker (17).

Weld V on target specimen (1) can be tested with the equipment representing the invention, in the following manner.

With target specimen (1) placed in the equipment in the appropriate position, the equipment is started. Controlled by the signal of central control unit (13), radiation source control circuit (7) operates radiation sources (2 and 3) in pulsed mode one after another. The X-ray images are picked up by video camera (4), and the video signal appearing at the output of the camera is displayed as a picture on video display (8), and is memorized— together with the marker signal provided by location signal source (6)—in image storage unit (9). The picture is compared by image comparator (11) with the flawless weld image in reference standard image storage (10). In the case of an identity, this is signal to central control unit (13) which documents this—together with the location signal (produced from the marker signal)—on printer (20) through special-purpose computer (15), and advances the equipment into the next test position with the use of actuation mechanizm (5). (This affects radiation sources 2 and 3, defect-spot marker 17 and video camera 4.)

When a difference (defect) is found by image comparator (11), this is signal led to central control unit (13) which starts the program of special-purpose computer (15) determining defect coordinates $X_o$, $Y_o$ and $Z_o$.

The data on the defect are received by special-purpose computer (15) from provisional image storage (12). The computed defect coordinates $X_o$, $Y_o$ and $Z_o$ are—together with the location signal and the identifier signal—printed by printer (20) and displayed (together with the picture of the weld) on defect display (19).

Defect storage (18) has the function of memorizing all data and images referred to a given defect.

On completion of the evaluation of a defect spot, the signal of special-purpose computer (15) causes central control unit (13) to start the marking of defect with the use of defect location marker (17) (e.g. a paint sprayer), and advances the equipment to the next test position with the use of actuation device (5).

Thus the equipment represented by our invention will test the weld seam step by step.

Image storage (9) will document the entire test enabling a reproduction at any time, together with the computations.

It is clear then that our invention offers the following advantages over the conventional procedure.

All procedures associated with photographic recording on a film are dispensed with (resulting in lower costs and a cut in time).

Significant pieces of information on the defect are available, which are not visible on a photograph, making for a simpler and quicker correction (or even rendering it unnecessary).

The distance of the defect from the surface of the weld can be determined directly.

The test can be documented in a very cheap procedure (enabling simple and inexpensive reproduction).

The exposure time, the loading and removal of film, the development process being eliminated, the test is speeded up considerably.

The application of the reference standard and the microprocessor results in a totally automatic evaluation.

What we claim is:

1. Video-radiographic process for the quality control of welds, wherein a weld seam is transilluminated, successively point by point, with X-ray or gamma ray, to produce electrical signals which represent a radiographic image of the weld and its environment; the image being stored for the display and used in the evaluation of a weld, wherein there are included the following improved steps:

(a) providing at least a pair of radiation sources of identical intensity, each directed toward the same portion of a new weld seam (V) at an angle, to transilluminate a portion of the weld area;

(b) positioning sources in a plane on the one side of the surface of weld seam (V), the plane being perpendicular with respect to a vertical axis (Y) and parallel with respect to both a transverse axis (X) and a longitudinal axis (Z), the (Z) axis extending along the length of the weld (V), the sources symmetrically disposed about the vertical axis (Y);

(c) positioning a target plate of a video camera in a plane disposed perpendicular to the vertical axis (Y), parallel to both the longitudinal axis (Z) and the transverse axis (X) on the other side of the surface of the weld seam to be irradiated, so that both radiation sources lie in a common plane spaced from and parallel to the plane of the target plate and separated by the weld seam (V);

(d) transilluminating the portion of the weld seam with the first radiation source operating in a pulsed mode to form a first radiographic still picture;

(e) converting the first radiographic still picture into electrical signals, noting the first picture's position along the seam, and storing the first picture and its position as a first image;

(f) transilluminating the same portion of the weld seam with the second radiation source operating in a pulsed mode to form a second radiographic still picture, noting the second picture's position along the seam, and storing the second picture and its position as a second image;

(g) repeating steps (a) through (f) along the entire length of the weld;

(h) forming a reference standard image using the above-mentioned steps (a) through (f) on a known flawless weld seam having the same characteristics and environment as the new weld; and (i) comparing each of the first and second images of the new weld with corresponding images of the previously obtained reference standard, obtained from the flawless weld having the same characteristics, to grade and determine the quality of the weld by comparison with the reference standard and to determine the position of any defects.

2. The process of claim 1 comprising the further steps of:

marking any defective weld detail on a workpiece under test with an identifier at the relevant defect coordinates.

3. The process of claim 2 comprising the further steps of:

aligning the axes of the first and second radiation sources (2 and 3), wherein the radiation sources each emit a beam of radiation, and the video camera in a common plane;

affixing sources and camera to actuation device and to control circuit to produce an alternating and pulsed operation thereof; and coordinating the operation of the process by connecting the output signal from actuation device as an input to a location signal source, connecting the output of signal source as an input to an image storage device, to a video display, to a computer and to a central control unit.

* * * * *